United States Patent
Habermann et al.

(10) Patent No.: US 8,276,423 B2
(45) Date of Patent: Oct. 2, 2012

(54) ROLLING MILL, ESPECIALLY A SWAG ROLLING MILL, FOR HEATED OPERATION

(75) Inventors: Andreas Habermann, Jülich (DE); Bernd Zieser, Netphen (DE); Gerhard Artel, Kirchhundem (DE)

(73) Assignee: SMS Siemag Aktiengesellschaft, Düsseldorf (DE)

( * ) Notice: Subject to any disclaimer, the term of this patent is extended or adjusted under 35 U.S.C. 154(b) by 170 days.

(21) Appl. No.: 10/550,793

(22) PCT Filed: Mar. 12, 2004

(86) PCT No.: PCT/EP2004/002573
§ 371 (c)(1),
(2), (4) Date: May 31, 2006

(87) PCT Pub. No.: WO2004/082859
PCT Pub. Date: Sep. 30, 2004

(65) Prior Publication Data
US 2006/0243015 A1    Nov. 2, 2006

(30) Foreign Application Priority Data
Mar. 22, 2003 (DE) .................................. 103 12 940

(51) Int. Cl.
*B21B 35/00* (2006.01)
*B21B 31/07* (2006.01)
*B21B 31/00* (2006.01)

(52) U.S. Cl. ........................................... 72/249; 72/237

(58) Field of Classification Search .................... 72/249, 72/237, 238, 239, 247
See application file for complete search history.

(56) References Cited

U.S. PATENT DOCUMENTS

| | | | | |
|---|---|---|---|---|
| 1,880,468 A | * | 10/1932 | Nye ................................ | 72/249 |
| 2,124,677 A | * | 7/1938 | Talbot ............................ | 72/248 |
| 2,513,058 A | * | 6/1950 | O'Malley et al. ............... | 72/249 |
| 2,575,231 A | * | 11/1951 | O'Malley ....................... | 72/239 |
| 2,870,664 A | * | 1/1959 | Lobkowitz ..................... | 72/247 |

(Continued)

FOREIGN PATENT DOCUMENTS
EP    0 491 785    12/1993
(Continued)

OTHER PUBLICATIONS
Patent Abstracts of Japan, vol. 0090, No. 03 (M-349), Jan. 9, 1985 & JP 59 156501 A (Sumitomo Jukikai Kogyo KK), Sep. 5, 1984.

*Primary Examiner* — Edward Tolan
*Assistant Examiner* — Lawrence J Averick
(74) *Attorney, Agent, or Firm* — Lucas & Mercanti, LLP; Klaus P. Stoffel

(57) ABSTRACT

The invention relates to a rolling mill, especially a swage rolling mill for heated operation, said rolling mill being provided with a pair of cylinders (3, 4) which are vertically arranged with the central axes thereof (5), can be adjusted in relation to each other, and are connected to at least one rotating drive (8) by means of cardan shafts (6; 7). The aim of the invention is to render the adjustment of the cylinders more favorable with lower displaced masses, to reduce friction and to improve lever arm relations. To this end, the rotating drive (8) for both cylinders (3; 4) is fixed beneath the mill floor level (2) and is respectively connected to a fixed gearbox (9) and the cardan shaft (6, 7) in a driving manner.

7 Claims, 1 Drawing Sheet

U.S. PATENT DOCUMENTS 2,927,488 A * 3/1960 Lothar .............................. 72/238
4,329,864 A * 5/1982 Ledebur ........................... 72/239
4,441,352 A * 4/1984 McDonagh et al. ............ 72/249

FOREIGN PATENT DOCUMENTS

| | | | |
|---|---|---|---|
| JP | 4819463 A | 3/1973 |
| JP | 59156501 A | 9/1984 |
| JP | 6418506 A | 1/1989 |
| SU | 132178 A1 | 1/1960 |
| SU | 293408 A1 | 1/1971 |
| SU | 1750757 A1 | 7/1992 |

* cited by examiner

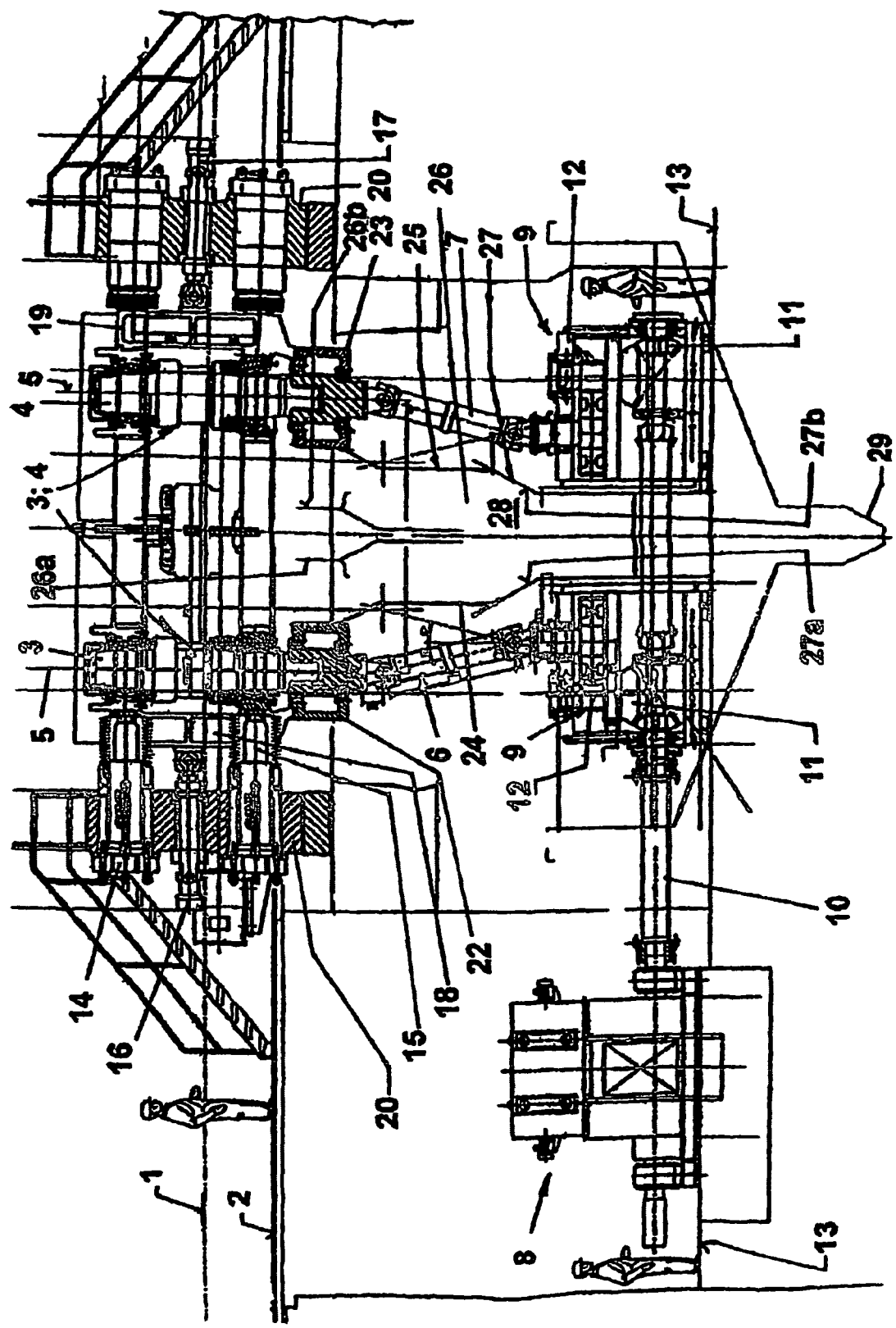

ROLLING MILL, ESPECIALLY A SWAG ROLLING MILL, FOR HEATED OPERATION

The invention concerns a rolling mill, especially an edging mill for hot operation, with a pair of rolls, which are arranged with their center axes vertical, can be adjusted relative to each other, and are connected to at least one rotary drive by means of cardan shafts.

Edging mills of this type are widely used as vertical rolling stands or edging stands with one or more crossheads, on which the heavy rotary drives for the rolls are supported (DE 1 602 177 A). The rolls can also be supported in horizontally cross-sliding cassettes (EP 0 491 785 B1). The cassette can also be vertically displaced (EP 0 493 430 B1). In accordance with an older proposal (DE 2 227 549 A), the rolls can be taken out in the upward direction vertically between the rotary drives.

The previously known rotary drives and adjustment drives have the disadvantage that this type of construction is technically complicated and not very reliable. Due to the large number of working action intervals of drive parts moving within each other, a great deal of wear occurs, and this results in high maintenance costs. The previously known drive arrangement is also associated with poor accessibility for maintenance work. Other disadvantages result from the sluggish adjustment response of the edging rolls, which are very heavy, cause tremendous friction and require large lever arms for the adjustment.

The objectives of the invention are to produce a more favorable adjustment response with lower displaced masses, to reduce friction, and to achieve better lever arm ratios.

In accordance with the invention, these objectives are achieved by stationary installation of the rotary drive for the two rolls below the mill floor level and by drive connection of the rotary drive with the respective cardan shaft by a stationary transmission. This allows faster and easier adjustment of the edging rolls, and, in addition, the displaced masses are smaller. The transmission is no longer moved together with the edging rolls but rather is anchored on the foundation or areas of the foundation. The lower displaced weight results in less friction. The lever arm relationships are also more favorable due to shorter adjustment devices. Furthermore, maintenance costs are reduced, and maintenance is easier, because the accessibility on the level of the mill floor and on the level of the foundation is easier. All of these advantages together result in greater plant availability and greater operational readiness, and this makes it possible to achieve optimized product quality.

In accordance with a refinement of the invention, the displaced masses can be further reduced by connecting the rotary drive to each cardan shaft by means of a continuous drive shaft and detached bevel gears on both sides and a spur gear.

In a further refinement, weight can also be locally adjusted by installing the adjustment drives on both sides of the vertical rolls above the mill floor level. The edging rolls can be freely lifted out upwardly between the adjustment drives and can be managed during installation.

In accordance with a refinement of the invention, the drive components located in the lower foundation area are protected by deflector plates that are mounted on the receivers for the heads of the cardan shafts and that can be moved together with the rolls.

In this connection, means for collecting and carrying the process waste materials to be removed are created by the formation of an essentially vertical, first shaft by the movable deflector plates.

In a refinement of this system, a second shaft that follows the first shaft is formed between the stationary spur gears of the cardan shafts by stationary deflector plates.

The protection of the lower-lying drive components can be further enhanced by the stationary deflector plates forming a trapezoidal or conical inlet that follows and is directly opposite the movable deflector plates.

The process waste materials that are collected in the first shaft and the second shaft can be further conveyed and disposed of by providing a trough-like collecting pit below the second shaft for carrying away dirt, scale, wastewater and the like.

The rolling mill is illustrated in the drawing and explained in greater detail below.

The sole drawing shows a front elevation of the rolling mill, in which the rolling stock moves perpendicularly to the plane of the drawing.

The rolling mill, which is shown in cross section perpendicular to the rolling direction, is constructed as an edging mill for hot operation. The direct deformation zone 1 lies above the mill floor level 2. The rolls 3 and 4 are arranged with the center axes 5 vertical and are connected to at least one rotary drive 8 by means of cardan shafts 6 and 7.

The special features, then, are the stationary installation of the rotary drive 8 for the two rolls 3 and 4 below the mill floor level 2 and the drive connection of the rotary drive 8 with a cardan shaft 6, 7 on each side by a stationary transmission 9.

For drive transmission, starting from the rotary drive 8 (which consists of a heavy electric motor), the driving power is transmitted by means of a continuous, rotatably supported drive shaft 10 and detached bevel gears on both sides (bevel gear steps) 11 and a one-step spur gear 12 on each cardan shaft 6 and 7.

In contrast to the installation of the rotary drive 8 below the mill floor level 2 on a foundation 13 built at a low level, the adjustment drives 14 and 15 are arranged on both sides of the vertical rolls 3, 4 above the mill floor level 2.

Between the paired adjustment drives 14 and 15 on both sides, hydraulically actuated piston-cylinder units 16 and 17 for roll crossheads 18, 19 are mounted in the columns 20 of the rolling stand.

Deflector plates 24 and 25 are mounted on receivers 22 and 23 for the heads of the cardan shafts 6, 7 and move together with the rolls 3, 4 when the rolls are adjusted. The pair of deflector plates 24, 25 forms a first, vertical shaft 26 or two adjacent partial shafts 26a and 26b.

A second shaft 27 is formed between the stationary spur gears 12 of the cardan shaft 6, 7. In consists of stationary deflector plates 27a, 27b.

The stationary deflector plates 27a, 27b form a trapezoidal or conical inlet 28 that follows and is directly opposite the movable deflector plates 24, 25.

A trough-like collecting pit 29 is formed in the foundation below the second shaft 27 for carrying away the collected dirt, scale, wastewater and the like.

LIST OF REFERENCE NUMBERS 1 direct deformation zone
2 mill floor level
3 roll
4 roll
5 center axis
6 cardan shaft
7 cardan shaft
8 rotary drive
9 stationary transmission 10 drive shaft
11 bevel gear
12 spur gear (spur gear step)
13 foundation
14 adjustment drive
15 adjustment drive
16 piston-cylinder unit
17 piston-cylinder unit
18 roll crosshead
19 roll crosshead
20 roll column
21
22 receiver for the head of a cardan shaft
23 receiver for the head of a cardan shaft
24 movable deflector plate
25 movable deflector plate
26 first shaft
26a partial shaft
26b partial shaft
27 second shaft
27a stationary deflector plate
27b stationary deflector plate
27 trapezoidal or conical inlet
28 trough-like collecting pit

The invention claimed is:

1. Edging mill for hot operation comprising a pair of rolls (3, 4) arranged with their center axes (5) vertical and adjustable relative to each other, each of said pair of rolls being connected to a stationary rotary drive motor (8) by means of a cardan shaft (6, 7), said stationary rotary drive motor (8) for the two rolls (3, 4) being installed below a mill floor level (2) and being in drive connection with a pair of stationary transmissions (9), each of said pair of stationary transmissions (9) being connected with one of said cardan shafts (6, 7), wherein movable deflector plates (24, 25) are mounted on receivers (22, 23) for the heads of the cardan shafts (6, 7) and are movable together with the rolls (3, 4), said deflector plates (24, 25) hanging and extending downward from said receivers (22, 23) and facing one another below said rolls (3, 4) and between said cardan shafts (6, 7) so as to protect said stationary transmissions (9) and said cardan shafts (6, 7) from process waste materials falling from above.

2. Edging mill in accordance with claim 1, wherein the rotary drive motor (8) is connected to each cardan shaft (6, 7) by means of a continuous drive shaft (10) with detached bevel gears (11) and spur gears (12).

3. Edging mill in accordance with claim 1, wherein adjustment drives (14, 15) are installed on both sides of the vertical rolls (3, 4) above the mill floor level (2).

4. Edging mill in accordance with claim 1, wherein the movable deflector plates (24, 25) form an essentially vertical, first shaft (26).

5. Edging mill in accordance with claim 4, wherein a second shaft (27) that follows the first shaft (26) is formed between spur gears (12) of the cardan shafts (6, 7) by stationary deflector plates (27a, 27b).

6. Edging mill in accordance with claim 5, wherein a collecting pit (29) is formed below the second shaft (27) for carrying away dirt, scale, and wastewater.

7. Edging mill for hot operation comprising a pair of rolls (3, 4) arranged with their center axes (5) vertical and adjustable relative to each other, each of said pair of rolls being connected to a stationary rotary drive motor (8) by means of a cardan shaft (6, 7), said stationary rotary drive motor (8) for the two rolls (3, 4) being installed below a mill floor level (2) and in drive connection with a pair of stationary transmissions (9), each of said pair of stationary transmissions (9) being connected with one of said cardan shafts (6, 7), wherein movable deflector plates (24, 25) are mounted on receivers (22, 23) for the heads of the cardan shafts (6, 7) and are movable together with the rolls (3, 4), said deflector plates (24, 25) hanging and extending downward from said receivers (22, 23) and facing one another below said rolls (3, 4) and between said cardan shafts (6, 7) so as to protect said stationary transmissions (9) and said cardan shafts (6, 7) from process waste materials falling from above, wherein the movable deflector plates (24, 25) form an essentially vertical, first shaft (26), wherein a second shaft (27) that follows below the first shaft (26) is formed between the spur gears (12) of the cardan shafts (6, 7) by stationary deflector plates (27a, 27b), and wherein the stationary deflector plates (27a, 27b) form a trapezoidal or conical inlet (28) that follows below and is directly opposite the movable deflector plates (24, 25).

* * * * *